United States Patent
Hart et al.

(10) Patent No.: US 7,182,955 B2
(45) Date of Patent: Feb. 27, 2007

(54) ABUSE-RESISTANT TRANSDERMAL DOSAGE FORM

(75) Inventors: John R. Hart, Stillwater, MN (US); Deanna L. Stebbings, Stillwater, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 463 days.

(21) Appl. No.: 10/744,996

(22) Filed: Dec. 23, 2003

(65) Prior Publication Data

US 2004/0219196 A1    Nov. 4, 2004

Related U.S. Application Data

(60) Provisional application No. 60/467,235, filed on Apr. 30, 2003.

(51) Int. Cl.
*A61K 9/70* (2006.01)

(52) U.S. Cl. .................. 424/449; 424/447

(58) Field of Classification Search ............. 424/443, 424/447, 448, 449
See application file for complete search history.

(56) References Cited

U.S. PATENT DOCUMENTS

| | | | |
|---|---|---|---|
| 1,602,344 A * | 10/1926 | Eagle ................ | 604/304 |
| 2,807,262 A * | 9/1957 | Lew ................. | 602/47 |
| 3,773,955 A | 11/1973 | Pachter et al. | |
| 4,457,933 A | 7/1984 | Gordon et al. | |
| 4,539,256 A | 9/1985 | Shipman | |
| 4,666,441 A * | 5/1987 | Andriola et al. ........ | 424/448 |
| 4,693,776 A | 9/1987 | Krampe et al. | |
| 4,917,688 A * | 4/1990 | Nelson et al. .......... | 604/306 |
| 5,066,494 A | 11/1991 | Becher | |
| 5,149,538 A | 9/1992 | Granger et al. | |
| 5,236,714 A | 8/1993 | Lee et al. | |
| 5,474,783 A | 12/1995 | Miranda et al. | |
| 5,585,111 A | 12/1996 | Peterson | |
| 5,756,117 A * | 5/1998 | D'Angelo et al. ........ | 424/449 |
| 5,985,317 A | 11/1999 | Venkateshwaran et al. | |
| 6,123,890 A | 9/2000 | Mazurek et al. | |
| 2002/0119187 A1 | 8/2002 | Cantor et al. | |
| 2003/0026829 A1 | 2/2003 | Venkatraman et al. | |
| 2005/0002997 A1 | 1/2005 | Howard et al. | |

FOREIGN PATENT DOCUMENTS

| | | |
|---|---|---|
| WO | WO 97/04835 | 2/1997 |
| WO | WO 00/01377 | 1/2000 |
| WO | WO 02/087482 A1 | 11/2002 |

(Continued)

OTHER PUBLICATIONS

Co-related U.S. Appl. No. 10/744,966, filed Dec. 23, 2003 entitled "Abuse-resistant Transdermal Dosage Form" (3M Case No. 57892US004).

*Primary Examiner*—Sharon Kennedy

(57) ABSTRACT

The invention comprises a transdermal dosage form comprising a active agent component comprising a polymeric matrix and an abusable drug substance, an overlay backing, a porous material, and an antagonist reservoir comprising an antagonist to the abusable drug substance. The porous material adjoins the antagonist reservoir and is in fluid communication with the skin-contacting surface defined by the active agent component. In one embodiment, the device comprises a barrier layer interposed between the active agent component and the antagonist reservoir.

30 Claims, 3 Drawing Sheets

FOREIGN PATENT DOCUMENTS

| | | |
|---|---|---|
| WO | WO 02/092059 A1 | 11/2002 |
| WO | WO 02/092060 A1 | 11/2002 |
| WO | WO 02/094172 A2 | 11/2002 |
| WO | WO 02/094173 A2 | 11/2002 |
| WO | WO 03/013433 A2 | 2/2003 |
| WO | WO 03/013525 A1 | 2/2003 |
| WO | WO 03/090729 A1 | 11/2003 |
| WO | WO 04/017941 | 3/2004 |

* cited by examiner

ABUSE-RESISTANT TRANSDERMAL DOSAGE FORM

CROSS REFERENCE TO RELATED APPLICATION

This application claims priority to U.S. Provisional Patent Application No. 60/467,235, filed Apr. 30, 2003.

The present invention relates to transdermal dosage forms which are useful for preventing or discouraging tampering, abuse or diversion of a dosage form containing an active pharmaceutical agent, such as an opioid. The present invention also relates to methods of treating a patient with such a dosage form.

BACKGROUND OF THE INVENTION

Transdermal drug delivery is a well known method for administering pharmaceuticals. The potential for abuse of certain pharmaceuticals, such as narcotics and other psychoactive drugs, is also well known. It is thus desirable when preparing a transdermal dosage form containing a substance with the potential for abuse to make such a device resistant to abuse or misuse. Although a transdermal dosage form is intended to deliver drug across the skin, misuse or abuse of such a dosage can take place by other modes, including oral, buccal, and intravenous.

Transdermal dosage forms comprising both a drug and an antagonist for the drug have been previously proposed. U.S. Pat. No. 5,236,714 (Lee et al.) describes a transdermal dosage form which comprises a mixture of a drug and an antagonist for the drug. U.S. Pat. No. 5,149,538 (Granger, et al.) describes a transdermal dosage form comprising an opioid permeable to the skin, an antagonist for the opioid releasable upon ingestion or solvent immersion of the dosage form, and an impermeable barrier means separating the opioid and the antagonist.

SUMMARY OF THE INVENTION

The present invention comprises a transdermal dosage form comprising an active agent component comprising a polymeric matrix and an abusable drug substance, an overlay backing, an adverse agent component (also referred to as an antagonist reservoir or an adverse agent reservoir), an antagonist reservoir comprising an antagonist to the abusable drug substance, and a porous medium adjoining the antagonist reservoir. The active agent component has a first, skin-contacting surface and a second surface opposed to the skin-contacting surface. The antagonist reservoir is interposed between the second surface of the active agent component and the backing. The porous medium is in fluid communication with the skin-contacting surface.

In one aspect, at least a portion of the antagonist is contained within the porous medium.

In another aspect, the invention further comprises a barrier layer adjoining the second surface of the active agent component.

In still another aspect, the porous medium comprises a polymeric film.

An object of the present invention is to provide a transdermal delivery device that is resistant to abuse through extraction of abusable substance from the device.

Another object of the present invention is to provide a transdermal delivery device that is resistant to abuse through ingestion of the device.

A further object of the present invention is to provide an abuse-resistant transdermal delivery device that comprises an antagonist for an abusable drug substance, wherein the antagonist is not delivered to the skin surface at a therapeutic level during intended use, but wherein the antagonist will be released from the dosage form along with the abusable drug substance during attempted abuse.

The above summary of the present invention is not intended to describe each disclosed embodiment or every implementation of the present invention. The Figures and the detailed description that follow more particularly exemplify illustrative embodiments.

BRIEF DESCRIPTION OF THE DRAWINGS

Preferred embodiments of the invention will now be described in greater detail below with reference to the attached drawings, wherein.

DETAILED DESCRIPTION OF THE INVENTION

The entire disclosure of U.S. Provisional Patent Application No. 60/467235, filed Apr. 30, 2003, is incorporated herein by reference.

Figure 1:
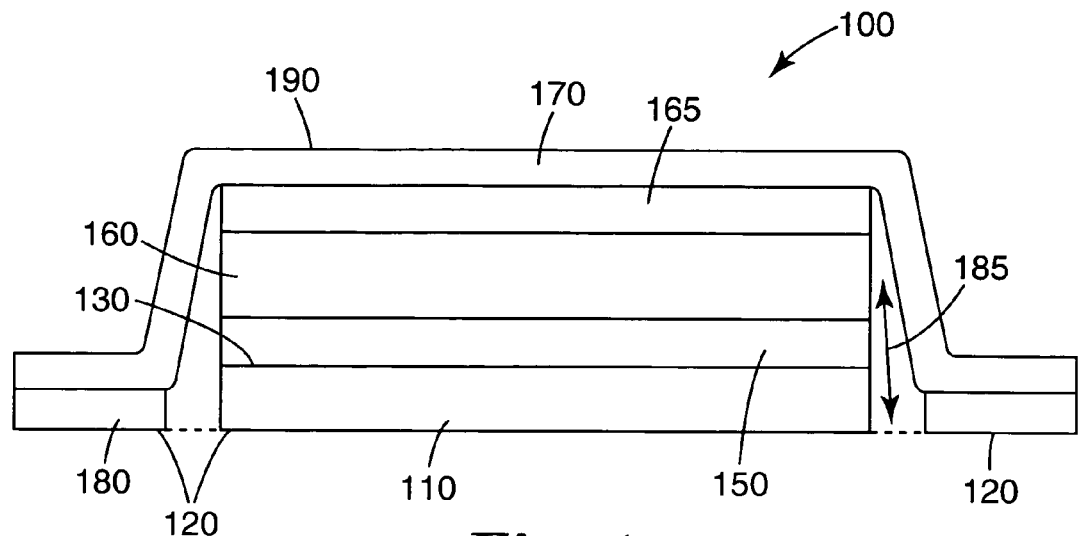
FIG. 1 shows a schematic cross-section of an embodiment of the present invention with a barrier between the active agent component and the adverse agent reservoir, and where the porous medium is adjacent to and adjoins the overlay backing.

In one embodiment, shown in FIG. 1, the present invention comprises a transdermal dosage form 100 comprising a active agent component 110 comprising a skin-contacting polymeric matrix and an active agent, an antagonist or adverse agent reservoir 160 comprising an antagonist to the active agent, a barrier 150, and a porous medium or material 165. The active agent component defines a proximal or skin-contacting surface 120 and has a distal surface opposed to, i.e., opposite to or in contraposition to, the proximal or skin-contacting surface 130. The barrier 150 is present as a component that is adjacent to and adjoins the distal surface of the active agent component 130 and the adverse agent reservoir 160. The porous medium or material 165 is adjacent to and adjoins the adverse agent reservoir 160. An overlay backing 170 is adjacent to and adjoins the porous medium 165 and provides an outer surface 190 of the dosage form 100.

The porous medium 165 is in fluid communication with the proximal surface 120. Fluid communication is meant to indicate that liquid may flow freely between the proximal surface 120 and the porous medium 165. That is, if the dosage form is immersed in a liquid such that the proximal surface is in contact with the liquid, then the liquid will also be able to contact the porous medium 165. The two-sided arrow 185 in FIG. 1 shows an area of fluid communication between the proximal surface 120 and the porous medium 165.

The active agent component 110 comprises a skin-contacting polymeric material and an active agent. The active agent is preferably dispersed homogeneously throughout the skin-contacting polymeric material, and more preferably dissolved within the skin-contacting polymeric material. The proximal or skin-contacting surface 120 should be sufficiently conformable when placed on a skin surface so as to make intimate contact with at least a portion of the skin surface. In one aspect, substantially all of the skin-contacting polymeric material at the skin-contacting surface 120 will make intimate contact with the skin surface. In one embodiment, the active agent component will have a thickness of no less than 10 µm, preferably no less than 20 µm, and more preferably no less than 50 µm. In another embodiment, the active agent component will have a thickness of no more than 250 µm, preferably no more than 200 µm, and more preferably no more than 150 µm.

In one embodiment, the active agent component of the present invention is a continuous, planar component in the form of a slab. In another embodiment, the active agent component may be structured or comprise channels, such that the polymeric material of the active agent component is discontinuous. Suitable active agent components that are either structured and/or comprise channels are described in copending U.S. Ser. No. 10/744,966 filed Dec. 23, 2003 entitled "Abuse-Resistant Transdermal Dosage Form" (File No. 57892US004), the disclosure of which is incorporated herein by reference in its entirety for all purposes. Suitable active agent components can include a plurality of strips, wherein the strips are separated by channels; an annular disk with a central channel filled with air; and a disk with a plurality of cylindrical air channels.

The skin-contacting polymeric material of the active agent component comprises a polymer, preferably a polymer selected from the group consisting of acrylates, natural rubbers, synthetic rubbers such as polyisobutylenes, polyisoprenes, styrenic block copolymers, polyvinylethers, silicone polymers, polyurethanes, and polyurethane-ureas. The polymers can be present alone or in combination. The skin-contacting polymeric material may optionally contain other additives, for example, penetration enhancers, tackifiers, plasticizers, anti-oxidants, colorants, and the like.

In one embodiment, the skin-contacting polymeric material may comprise a pressure-sensitive adhesive. Preferred pressure-sensitive adhesives for use in dosage forms of the invention include acrylates, polyisobutylenes, silicone polymers, and mixtures thereof. Examples of useful polyisobutylene pressure-sensitive adhesives are described in U.S. Pat. No. 5,985,317 (Venkateshwaran et al.), the disclosure of which is incorporated herein by reference in its entirety for all purposes. Examples of useful acrylate and silicone polymer pressure-sensitive adhesives, and mixtures thereof, are described in U.S. Pat. No. 5,474,783 (Miranda), the disclosure of which is incorporated herein by reference in its entirety for all purposes.

Acrylate polymers and copolymers are particularly preferred pressure-sensitive adhesives. Examples of suitable monomers for use in acrylate copolymers include alkyl acrylates, such as isooctyl, 2-ethylhexyl, n-butyl, ethyl, methyl, and dimethylhexyl, and alkyl methacrylates, such as lauryl, isodecyl, and tridecyl. Monomers containing functional groups, such as carboxylic acid, hydroxy, amide, and amino may also be incorporated into an acrylate copolymer. Examples of suitable monomers containing functional groups include acrylic acid, hydroxyalkyl acrylates containing 2 to 4 carbon atoms in the hydroxyalkyl group, acrylamide, N-vinyl-2-pyrrolidone, vinyl acetate, and alkoxyethyl acrylate.

Acrylate copolymers may optionally further comprise a substantially linear macromonomer copolymerizable with the other monomers. Suitable macromonomers include polymethylmethacrylate, styrene/acrylonitrile copolymer, polyether, and polystyrene macromonomers. Examples of useful macromonomers and their preparation are described in U.S. Pat. No. 4,693,776 (Krampe et al.), the disclosure of which is incorporated herein by reference in its entirety for all purposes.

The active agent of the present invention may be any drug substance that is capable of being abused. Many drugs have a potential for abuse, and include, for example, narcotics, such as morphine, fentanyl, codeine, sufentanil, and oxycodone; psychostimulants, such as amphetamine, methamphetamine, and methylphenidate; methoxy substituted amphetamines, such as 3,4-methylenedioxymethamphetamine (MDMA); and benzodiazepines, such as diazepam, oxazepam, and lorazepam.

The active agent will be present in an amount such that the composition delivers a therapeutically effective amount for the condition being treated. This amount will vary according to the type of drug used, the condition to be treated, the amount of time the composition is allowed to remain in contact with the skin of the subject, and other factors known to those of skill in the art.

For example, information on dosing and the amount of opioid agonist active agent present in a transdermal dosage form is set forth in U.S. Published Patent Application No. 2002/0119187 A1, filed Sep. 26, 2001, entitled "Composition for the Transdermal Delivery of Fentanyl" by Cantor et al. and U.S. Published Patent Application No. 2003/0026829 A1, filed Mar. 15, 2002, entitled "Transdermal Administration of Fentanyl and Analogs Thereof" by Venkatraman et al., each of which is incorporated herein by reference in its entirety for all purposes. In one embodiment, the amount of active agent present in the transdermal drug delivery composition of the invention is greater than about 0.01 wt-% and preferably greater than about 1.0 wt-%, based on the total weight of the composition. In another embodiment, the amount of active agent present in the transdermal drug delivery composition of the invention is less than about 40 wt-% and preferably less than about 20.0 wt-%, based on the total weight of the composition.

In FIG. 1, the adverse agent reservoir 160 is connected on one side to a barrier 150 layer and on the other side to the porous medium 165. The reservoir may be a polymeric material, porous film, or other component suitable for containing an adverse agent. Preferably, the adverse agent component 160 is capable of containing a sufficient amount of antagonist to blunt or block at least one biological effect of the active agent or to cause at least one unpleasant side effect in a patient or animal which has absorbed the total amount of active agent in the dosage form 100. This amount can vary according to the type of antagonist used, the amount and type of active agent used, and the mode of abuse.

Furthermore, the adverse agent component 160 should be capable of releasing antagonist when it comes into contact with extraction solvents, such as water, ethanol, ether, or mixtures thereof.

Suitable polymeric materials or matrices for use in the adverse agent component include, but are not limited to, acrylates, natural rubbers, synthetic rubbers such as polyisobutylenes, polyisoprenes, styrenic block copolymers, polyvinylethers, silicone polymers, polyurethanes, and polyurethane-ureas. The adverse agent or antagonist is preferably dispersed homogeneously throughout the polymeric matrix. In one aspect, the antagonist is dissolved within the polymeric matrix. In another aspect, solid crystals of antagonist are dispersed throughout the polymeric matrix. Preferably, the polymeric matrix is a pressure sensitive adhesive. Suitable pressure-sensitive adhesives include those suitable for use as the polymeric material of the active agent component. Additionally, pressure-sensitive adhesives that are not suitable for direct skin contact can be suitable for use as the polymeric material of the adverse agent reservoir.

The adverse agent component can also comprise a porous medium or material, such as a woven fabric, porous or microporous film, or other open, mesh-like material, wherein at least a portion of the pores contain adverse agent or antagonist. The antagonist can be present within the pores in any form, including but not limited to a liquid, a gel or a solid, such as a solid crystalline or powdered material. Alternatively, the antagonist may be mixed with a carrier, such as a viscous liquid or semi-solid material. Examples of suitable films include, for example, microporous films formed by extruding polyethylene or polypropylene with mineral oil as described in U.S. Pat. No. 4,539,256 (Shipman), the disclosure of which is incorporated herein by reference.

The antagonist to the active agent is a compound or composition that acts to prevent, diminish, or delay the pharmacological effects of the active agent, or otherwise acts to deter potential abuse. Antagonists may include, for example, narcotic antagonists, such as naltrexone, naloxone and nalbuphine; bitter tasting substances; emetics, or nauseants. Narcotic antagonists, most preferably naltrexone, are preferably used in conjunction with abusable narcotics. The antagonist will preferably act to blunt or block at least one biological effect of the active agent or to cause at least one unpleasant side effect in a patient or animal which has absorbed the active agent.

The barrier 150 shown in FIG. 1 is a component adjacent to and adjoining the distal surface of the active agent component 130 on one side and the adverse agent reservoir 160 on the other side. The barrier is impermeable to diffusion of active agent and antagonist.

In relation to the present invention, impermeability of the barrier to diffusion of active agent and antagonist is defined such that only insignificant amounts, and preferably none, of active agent or antagonist are able to diffuse across the barrier during ordinary use or storage of the device. The precise amount that is insignificant will vary depending on the particular application for the dosage form, but it will be understood to include any amounts of active agent or antagonist that do not significantly alter the therapeutic effect of the dosage form (e.g., the active agent concentration in the active agent component does not change significantly due to diffusion of active agent across the barrier and a pharmacologically effective amount of antagonist does not diffuse across the barrier and into the active agent component). Any insignificant amounts of active agent that diffuse across the barrier are preferably less than 5%, more preferably less than 1%, and most preferably less than 0.1% by weight of the total active agent in the dosage form. Any insignificant amounts of active agent or antagonist that may diffuse across the barrier will preferably do so over a time period greater than 1 month, more preferably greater than 6 months, and most preferably greater than 2 years.

Suitable barriers can be films comprised of but not limited to, for example, polyesters, such as polyethylene terephthalate; polypropylenes; and polyethylenes, such as high density polyethylene. Multi-layered films, such as polyethylene terephthalate-aluminum-polyethylene composites are also suitable. The barrier is preferably a continuous film layer.

In one embodiment, the barrier thickness is more than 1 μm, preferably more than 10 μm, and more preferably more than 20 μm. In another embodiment, the barrier thickness is less than 100 μm, preferably less than 80 μm, and more preferably less than 60 μm.

Dissolvable films, such as polyvinyl alcohol or modified polyvinyl alcohols may be suitable, as long as the films are impermeable to diffusion of abusable drug substance and antagonist as defined above. Suitable barriers may also include porous or microporous films.

Barriers of the present invention can also comprise an impermeable surface coating applied to one of the other surfaces present in the device, such as the distal surface of the active agent component, which is opposed to the skin-contacting surface, or the surface of the adverse agent reservoir facing the active agent component. Examples of suitable coatings include fluoropolymers, such as polymers or copolymers of tetrafluoroethylene, hexafluoropropylene, and/or vinylidene fluoride. Terpolymers of tetrafluoroethylene, hexafluoropropylene, and vinylidene fluoride, such as Dyneon™ fluorothermoplastic THV are preferred coatings. The thickness of impermeable surface coatings is preferably between 0.5 and 10 μm thick, more preferably between 1 and 5 μm thick, and most preferably between 2 and 4 μm thick. In one aspect, the barrier is a thin coating on the surface of a microporous film reservoir.

In one embodiment, the barrier of the present invention is a continuous, planar component in the form of a slab. In another embodiment, the barrier may be patterned or comprise channels, such that the barrier is discontinuous. Suitable barriers comprising channels are described in copending U.S. Ser. No. 10/744,966 filed Dec. 23, 2003 entitled "Abuse-Resistant Transdermal Dosage Form" (File No. 57892US004). Suitable barriers can include a plurality of strips wherein the strips are separated by channels, an annular disk with a central channel filled with air, and a disk with a plurality of cylindrical air channels.

As shown in FIG. 1, an overlay backing 170 extends beyond the area of the porous medium 165, adverse agent or reservoir component 160, barrier 150, and active agent component 110 to a sufficient extent to allow the peripheral edge of overlay backing 170 to contact the skin surface of a patient.

The peripheral edges of the overlay backing 170 can be coated with an overlay pressure sensitive adhesive (PSA) 180 that is used to secure the edges of the overlay backing 170 to a skin surface. Any pressure sensitive adhesive suitable for use in skin-contacting applications, as previously described, can be used as the overlay PSA 180. Typical examples of flexible backing materials employed as conventional tape backings which may be useful for the present invention include those made polymer films such as polypropylene; polyethylene, particularly low density polyethylene, linear low density polyethylene, metallocene polyethylenes, and high density polyethylene; polyvinyl chloride; polyester (e.g., polyethylene terephthalate); ethylene-vinyl acetate copolymer; polyurethane; cellulose acetate; and ethyl cellulose. Backings that are laminated or layered, such as polyethylene terephthalate-aluminum-polyethylene composites, are also suitable. Fabrics and non-wovens are also suitable. In a preferred embodiment, the overlay backing is a continuous polymeric film that prevents ingress of external moisture into the adverse agent component from activities such as showering and bathing. Examples of such continuous films include polyurethane, polyethylene, and polyester.

Figure 3:
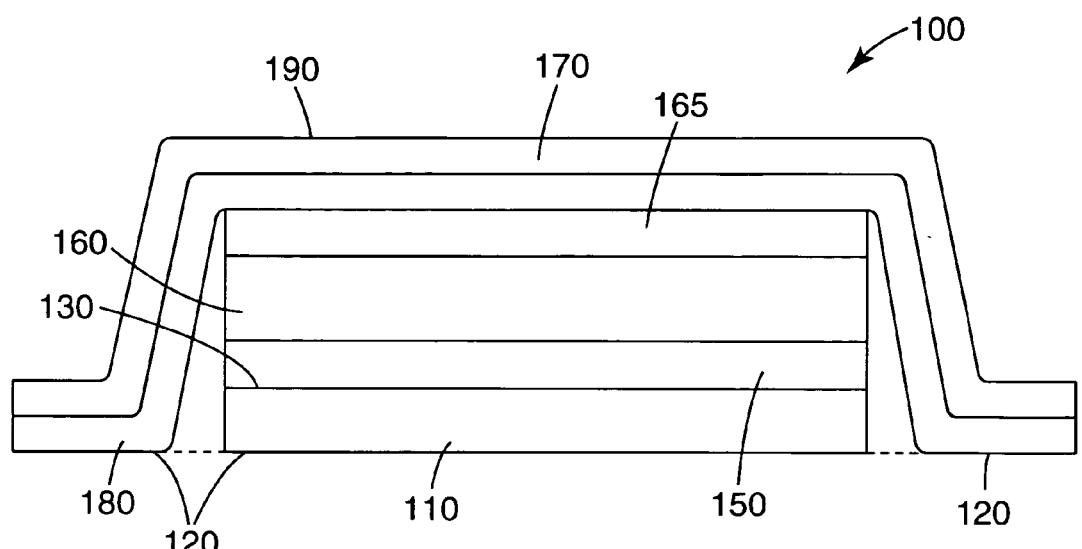
FIG. 3 shows a schematic cross-section of an embodiment of the present invention similar to FIG. 1, except that the overlay PSA is coated uniformly across the overlay backing, instead of being present only at the outer edges of the overlay backing.

As shown in FIG. 3, the overlay backing 170 is continuously coated with an overlay pressure sensitive adhesive (PSA) 180 that is used to secure the edges of the overlay backing 170 to a skin surface. In this embodiment, the overlay PSA 180 serves a dual purpose. The area of the overlay PSA 180 extending beyond the area of the porous medium 165, adverse agent reservoir 160, barrier 150, and active agent component 110 serves to secure the dosage form to a skin surface. The area of the overlay PSA 180 that does not extend beyond the adverse agent or reservoir component 160 provides secure lamination of the overlay backing 170 to the porous medium 165. An optional barrier component may be placed between the overlay PSA 180 and the porous medium 165 in order to prevent any interaction between the overlay PSA 180 and the porous medium 165. This optional component is preferably a flexible backing material as described above and is more preferably a polyethylene film.

The porous medium 165 is a material or construct characterized in that it has openings that allow the passage or absorption of liquids. Examples of a porous medium include microporous films, such as microporous films formed by extruding polyethylene or polypropylene with mineral oil as described in U.S. Pat. No. 4, 539,256 (Shipman); fibrous webs; woven fabrics and textiles; open-cell foams; grooved films; and other open, mesh-like materials. A porous medium may have the appearance of a solid matrix characterized by a fine network of microscopic openings. In another aspect, it may be a structured slab or film having channels or grooves that allow the passage of liquid. It should be understood that certain structures with open channels or grooves will act as a porous medium when the open channels or grooves are adjoining another layer, such as the antagonist reservoir.

As shown in FIG. 1, the porous medium 165 is adjacent to and adjoins the adverse agent reservoir 160, such that if the dosage form 100 is immersed in a solvent bath, then the porous medium 165 allows for fluid communication of the solvent with the top surface of the reservoir 160. The porous medium 165 may align with the adverse agent reservoir 160. Alternatively, the porous medium may extend beyond the area of the adverse agent reservoir 165 and may fill part or all of the void area shown in FIG. 1 where the fluid communication between the porous medium 165 and the skin-contacting surface 120 takes place.

Figure 4:
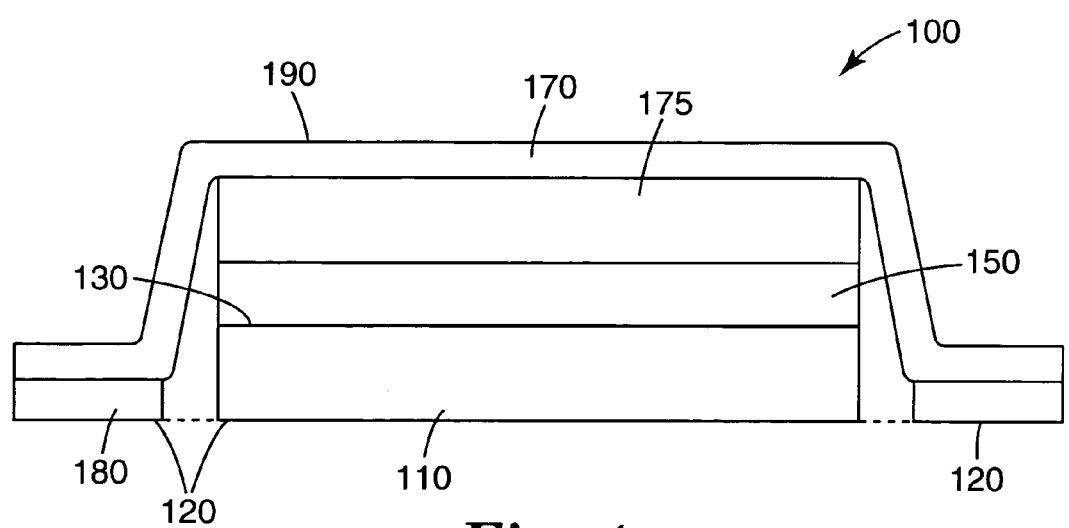
FIG. 4 shows a schematic cross-section of an embodiment of the present invention with a barrier between the active agent component and the adverse agent reservoir, and where the porous medium serves as the adverse agent reservoir.

In an alternative embodiment, shown in FIG. 4, the porous medium and adverse agent reservoir may form a single integral component 175 of the dosage form. That is, the porous medium may serve as the carrier matrix of the adverse agent reservoir.

Figure 2:
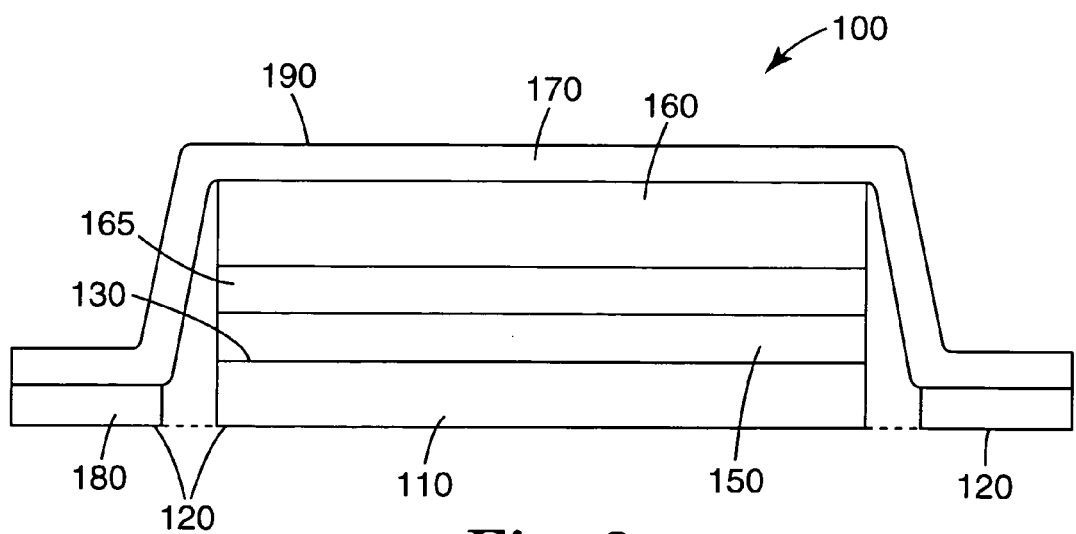
FIG. 2 shows a schematic cross-section of an embodiment of the present invention with a barrier between the active agent component and the porous medium, and where the adverse agent reservoir is adjacent to and adjoins the overlay backing.

As shown in FIG. 2, the adverse agent reservoir 160 may be adjacent to and adjoin the overlay backing 170, and the porous medium 165 is interposed directly between the adverse agent reservoir 160 and the barrier 150. Furthermore, the porous medium need not be present as a distinct component in contact with a major surface of the adverse agent reservoir, so long as the porous medium is adjacent to the adverse agent reservoir and is in fluid communication with the active agent component. Thus, for example, the porous medium may be an annular disk surrounding a central adverse agent reservoir, an interpenetrating network within the adverse agent reservoir, or other like configurations.

Figure 5:
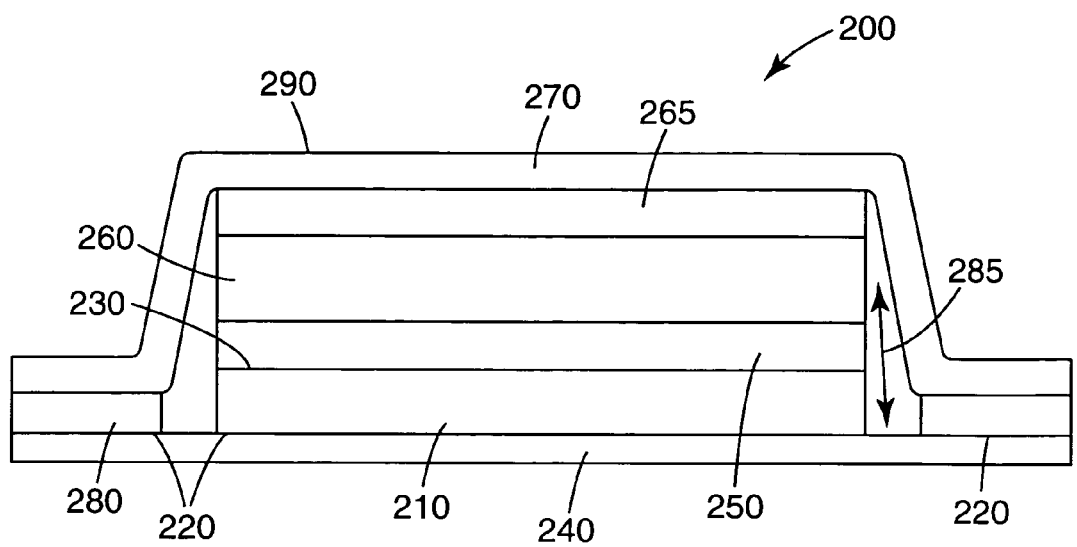
FIG. 5 shows a schematic cross-section of an embodiment of the present invention with a barrier between the active agent reservoir and the adverse agent reservoir, and where the active agent reservoir is adjacent to and adjoins the barrier and the release liner.

In another embodiment, shown in FIG. 5, the present invention comprises a transdermal dosage form 200 comprising a release liner 240, an overlay backing 270, an active agent reservoir 210, an adverse agent reservoir 260 comprising an antagonist to the active agent, a barrier 250, and a porous medium 265. The barrier 250 is present as a component that is adjacent to and adjoins the active agent reservoir 210 and the adverse agent reservoir 260. The porous medium 265 adjoins the adverse agent reservoir 260. The overlay backing 270 adjoins the porous medium 265 and provides an outer surface 290 of the dosage form 200. As shown, the release liner 240 has a release surface 245 adjacent to and adjoining the active agent reservoir 210. In alternative embodiments, one or more components, such as a skin-contacting adhesive and/or a rate-limiting membrane may be interposed between the active agent reservoir 210 and the release surface 245. The active agent within the active agent reservoir 210 is in diffusional communication with the release surface. Diffusional communication is understood to mean that a substance, such as an active agent, is able to diffuse from one area to another by passing through or across one or more solid or liquid media.

The porous medium 265 is in fluid communication with the release surface 245. Fluid communication is meant to indicate that liquid may flow freely between the skin-contacting surface 220 and the release surface 245. That is, liquid present on the exposed areas of the release surface 245 will also be able to contact the porous medium 265. The two-sided arrow 285 shows the area of fluid communication between the release surface 245 and the porous medium 265.

Figure 6:
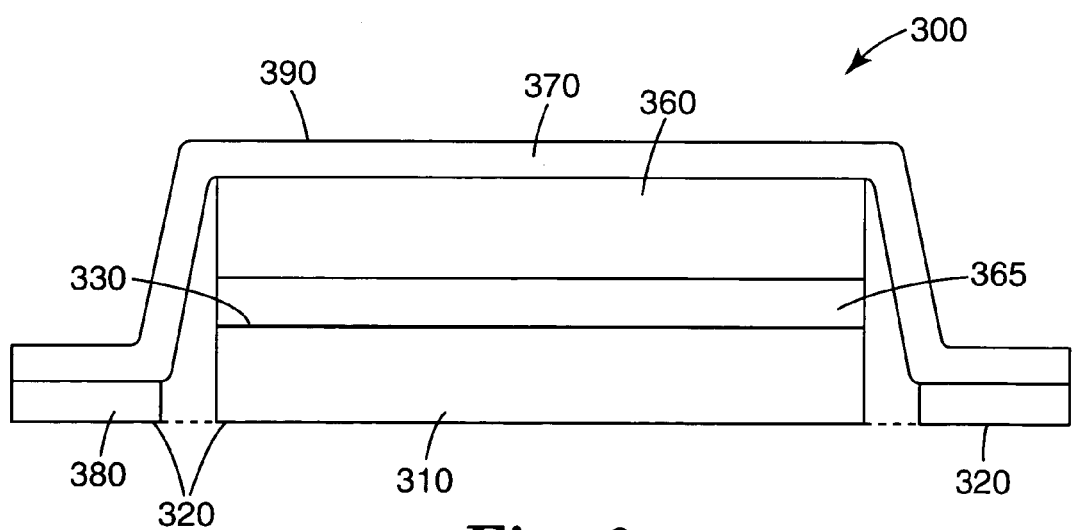
FIG. 6 shows a schematic cross-section of an embodiment of the present invention where the porous medium is adjacent to and adjoins the active agent component.

In another embodiment, shown in FIG. 6, the present invention comprises a transdermal dosage form 300 comprising an active agent component 310 comprising a skin-contacting polymeric material and an active agent, an adverse agent reservoir 360 comprising an antagonist to the active agent, and a porous medium 365. The active agent component defines a proximal, skin-contacting surface 320 and has a distal surface opposed to the skin-contacting surface 330. The porous medium 365 is adjacent to and adjoins the distal surface opposed to the skin-contacting surface 330 and the adverse agent reservoir 360. An overlay backing 370 with an overlay PSA 380 is adjacent to and adjoins the adverse agent reservoir 360 and provides an outer surface 390 of the dosage form 300.

The porous medium 365 is in fluid communication with the skin-contacting surface 320. Fluid communication is meant to indicate that liquid may flow freely between the skin-contacting surface 320 and the porous medium 365. That is, if the device is immersed in a liquid such that the skin-contacting surface is in contact with the liquid, then the liquid will also be able to contact the porous medium 365.

In this embodiment, antagonist in the adverse agent reservoir 360 and active agent in the active agent component 310 should not be in diffusional communication with each other.

The active agent components may comprise a number of additional components in addition to a polymeric material and an abusable drug substance. Additional components of the active agent component can include skin penetration enhancers, drug solubilizers, plasticizers, anti-oxidants, colorants, and the like.

Examples of excipients useful as skin penetration enhancers or solubilizers in transdermal drug delivery systems include $C_8$–$C_{24}$ fatty acids such as isostearic acid, octanoic acid, and oleic acid; $C_8$–$C_{24}$ fatty alcohols such as oleyl alcohol and lauryl alcohol; lower alkyl esters of $C_8$–$C_{24}$ fatty acids such as ethyl oleate, isopropyl myristate, butyl stearate, and methyl laurate; monoglycerides of $C_8$–$C_{24}$ fatty acids such as glyceryl monolaurate; tetraglycol (tetrahydrofurfuryl alcohol polyethylene glycol ether); tetraethylene glycol (ethanol,2,2'-(oxybis(ethylenoxy))diglycol); polyethylene glycol; propylene glycol; N,N-dimethyldodecylamine-N-oxide; terpenes, such as d-limonene, menthol, and terpineol.

In compositions of the active agent component of the present invention the skin penetration enhancers, drug solubilizers, plasticizers, and other additives are dispersed, preferably substantially uniformly, and more preferably dissolved in the composition. Where the additive is a penetration enhancer, it is present in an amount that enhances drug permeation through the skin compared to a like composition not containing the penetration enhancer(s) when this phenomenon is measured using a standard skin penetration model, such as in U.S. Pat. No. 5,585,111 (Peterson), the disclosure of which is herein incorporated by reference. The total amount of penetration enhancer and solubilizer will generally be less than 40% by weight, preferably less than 30% based on the total weight of the composition.

Active agent component compositions of the invention can be prepared by combining the polymer matrix, active agent, and optional additives, such as penetration enhancers, with an organic solvent (e.g., ethyl acetate, isopropanol, methanol, acetone, 2-butanone, ethanol, toluene, alkanes, and mixtures thereof) to provide a coating composition. The mixture is shaken or stirred until a homogeneous coating composition is obtained. The resulting composition is then applied to a release liner using conventional coating methods (e.g., knife coating or extrusion die coating) to provide a predetermined uniform thickness of coating composition. Non-continuous or discontinuous coatings may be prepared using methods such as stripe coating, screen printing, and ink-jet printing.

Dosage forms of the present invention typically comprise a release liner that covers and protects the skin-contacting surface prior to use by a patient. Suitable release liners include conventional release liners comprising a known sheet material such as a polyester web, a polyethylene web, a polystyrene web, or a polyethylene-coated paper coated with a suitable fluoropolymer or silicone based coating. The release liner that has been coated with the composition is then dried to prepare the active agent component and laminated to the other layers of the device using conventional methods.

When the adverse agent or reservoir component comprises a pressure-sensitive adhesive or similar polymeric material or matrix, then the adverse agent component compositions of the invention can be prepared using methods similar to those for preparing the active agent component, with the exception that an adverse agent or antagonist is used in place of the active agent to prepare the coating composition. Alternatively the adverse agent reservoir can comprise a porous medium, such as a porous or microporous film. The antagonist can be dissolved in an impregnating solvent and the porous or microporous film is soaked in the solvent for a sufficient period of time to allow the antagonist to penetrate the pores of the film. The solvent is then dried leaving the antagonist dispersed throughout the film.

Depending on the particular construction of the dosage form, the dried active agent component, adverse agent reservoir, porous medium, overlay backing, and optional barrier are laminated together using conventional methods. Optional tie layers or heat may be used to connect one or more of the layers. Alternatively, the active agent component compositions and adverse agent reservoir compositions may be directly coated onto one of the other layers of the device, dried, and subsequently laminated to another layer or release liner.

An overlay backing is laminated to the surface of either the porous medium or the adverse agent reservoir to provide an upper surface of the device, optionally using heat or an additional tie layer to ensure adequate contact.

One skilled in the art will appreciate that it may be preferred to vary the order of lamination steps depending on the types and thickness of the layers comprising the device.

The transdermal dosage forms of the invention can be made in the form of an article such as a tape, a patch, a sheet, a dressing or any other form known to those skilled in the art. Generally, the dosage form will be in the form of a patch of a size suitable to deliver a preselected amount of drug through the skin.

Generally, the dosage form will have a surface area greater than 5 cm$^2$, preferably greater than 10 cm$^2$. Generally, the device will have a surface area of less than 100 cm$^2$, preferably less than 40 cm$^2$.

Dosage forms of the present invention are typically packaged individually in a foil-lined pouch for storage. Dosage forms of the present invention may alternatively be provided in a rolled or stacked form suitable for use with a dispensing apparatus.

EXAMPLES

In Vitro Skin Permeation Test Method

The skin permeation data given in the examples below was obtained using the following test method. The test samples were transdermal devices having a total area of 5.0 cm$^2$ and an active drug-containing area of 2.0 cm$^2$ was used as the test sample. The release liner was removed, and the patch was applied to human cadaver skin and pressed to cause uniform contact with the skin. The resulting patch/skin laminate was placed patch side up across the orifice of the lower portion of a vertical diffusion cell. The diffusion cell was assembled and the lower portion filled with 25 mL of warm (32° C.) receptor fluid (0.1 M phosphate buffer, pH 6.8) so that the receptor fluid contacted the skin. The sampling port was covered except when in use.

The cells were maintained at 32±2° C. throughout the course of the experiment. The receptor fluid was stirred by means of a magnetic stirrer throughout the experiment to assure a uniform sample and a reduced diffusion barrier on the dermal side of the skin. The entire volume of receptor fluid was withdrawn at specified time intervals and immediately replaced with fresh fluid. The withdrawn fluid was filtered through a 0.45 μm filter. The last 1–2 mL were then analyzed for fentanyl using conventional high performance liquid chromatography methods (Column: Zorbax SB AQ, 50×4.6 mm, 5 μm particle size; Mobile phase: 3–20% isopropanol in 22 mM phosphate buffer; Flow Rate: 1.5 mL/min; Detector: uv at 230 nm; Injection Volume: 10 μL; Run time: 6 minutes). The cumulative amount of fentanyl penetrating through the skin was calculated and reported as μg/cm$^2$. Unless noted, the results are reported as the average of 8 replicates.

Extraction Method

The test samples were 3.3 cm$^2$ transdermal patches. The extraction solution was chosen from one of the following solutions: buffered saline (PBS, 0.06 M phosphate buffer for pH 6.5, 0.5 M sodium chloride); diethyl ether (reagent grade with BHT preservative); deionized (DI) water; ethanol (USP, absolute); ethyl acetate (HPLC grade).

The patch and a 15 mL extraction solution were added into a 40 mL vial. The sealed vial was vigorously shaken with a wrist-action shaker (Burrel, Model 75, speed setting: 10). At fixed time intervals of 5, 15, and 30 minutes aliquots were removed. Each aliquot was placed into an analysis vial. If the extraction solvent was ethyl acetate or ether, then it was evaporated to dryness and methanol (HPLC grade) was added to the sample and mixed. Samples were assayed for active drug substance by reverse-phase HPLC.

Mechanical Separation Method

The test samples were 20.0 cm$^2$ overlay transdermal patches (active area 10.5 cm$^2$). Four individuals tested a single patch of each type. The testers were given diagrams indicating the individual layers of the patch. The testers were also provided with a scalpel, tweezers, and adhesive tape to use as tools. Each tester was given a one-hour time period and instructed to mechanically separate the patch in an attempt to separate the fentanyl from the naltrexone. Separated material believed to contain fentanyl and to be free of naltrexone was placed into 40 mL vials, extracted with approximately 5 mL of methanol, and tested by HPLC for both fentanyl and naltrexone content. The results are reported as the average amount of fentanyl recovered from each patch, the average amount of naltrexone recovered from each patch, and the ratio of fentanyl to naltrexone recovered.

Copolymer A. Preparation of Isooctyl Acrylate/2-Hydroxyethyl acrylate/Elvacite™ 1010 Copolymer Solution A master batch was prepared by combining isooctyl acrylate (714.00 g), 2-hydroxyethyl acrylate (523.00 g), polymethylmethacrylate macromonomer (52.00 g) of ELVACITE™ 1010 available from ICI Acrylics), 2,2'-azobis (2-methylbutyronitrile) (2.60 g), ethyl acetate (1245.50 g) and isopropanol (45.50 g). The resulting solution was divided in equal portions and placed into six 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath, unsealed, diluted with 76 g methanol per bottle, mixed until homogenous, and recombined into a 1 gallon (3.8 L) glass jar. The percent solids of the resultant copolymer was 40.5%. The inherent viscosity, I.V., (of a 0.15 g/dL solution of polymer in ethyl acetate measured at 27° C.) was 0.77 dL/g.

Copolymer B. Preparation of 2-Ethylhexyl Acrylate/Dimethylaminoethyl Acrylate Methyl Chloride Quaternary/Methoxy Polyethylene Glycol 400 Acrylate Copolymer Solution A master batch was prepared by combining 2-ethylhexyl acrylate (234 g), dimethylaminoethyl acrylate methyl chloride quaternary (90 g), methoxy polyethylene glycol 400 acrylate (54 g), methanol (200.84 g) and acetone (221.14 g). The resulting solution was divided in equal portions and placed into two 1 quart (0.95 L) amber glass bottles. The bottles were purged for 2 minutes with nitrogen at a flow rate of 1 L per minute. The bottles were sealed and placed in a rotating water bath at 57° C. for 24 hours. At 24 hours the bottles were removed from the rotating water bath and cooled. Methanol (50 g) and acetone (50 g) were added to each bottle and mixed until homogeneous. The resulting solutions were then treated with radical scavengers for an additional 6 hours at 57° C. to reduce the amount of remaining residual monomers. The resulting copolymer solutions in the two bottles were recombined into a 1 gallon (3.8 L) glass jar. The percent solids of the resultant copolymer was 36.3%. The Brookfield viscosity was 835 centipoise.

Example 1

A transdermal dosage form according to FIG. 3 was prepared as follows.

Fentanyl (2.40 g) was added to methanol (2.80 g) and mixed until all of the fentanyl was dissolved. To this solution, copolymer (32.5 g of a 38.8% solids solution of isooctyl acrylate/2-hydroxyethyl acrylate/Elvacite™ 1010 with an inherent viscosity of 0.63 dL/g prepared according to the general procedure described for Copolymer A above) was added and mixed until a uniform coating formulation was obtained. The coating formulation was knife coated onto a silicone release liner. The coated liner was oven dried for 4 minutes at 110° F. (43° C.), for 4 minutes at 185° F. (85° C.), and for 2 minutes at 200° F. (93.3° C.). The resulting dried coating weight was 7.3 mg/cm$^2$. The resulting coating contained 16.0 percent fentanyl. The coated liner was laminated onto the polyethylene terephthalate side of a 2.0 mil (51 μm) thick laminate film of polyethylene terephthalate and ethylene vinyl acetate (Scotchpak™ 9732, 3M, St. Paul, Minn.).

An adverse agent or reservoir component was prepared as follows. Naltrexone base (3.01 g) was added to copolymer (59.5 g of a solution of a 28.6% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was 14.4 mg/cm$^2$. The resulting coating contained 15.0 percent naltrexone. The coated liner was laminated to the ethylene vinyl acetate side of the dried fentanyl coating prepared above to form a multilaminate construction. The resulting multilaminate construction was converted into 2.0 cm$^2$ parts.

A 1.0 ounce/yd² (33.9 g/m²) basis weight porous polyethylene apertured film (Style 6007, Polymer Group, Inc., North Charleston, S.C.) was ultrasonically welded to a 3.0 mil (76 μm) thick polyethylene film (CoTran™9720, 3M, St. Paul, Minn.) using a 20 kHz Dukane ultrasonic welder with a 3 inch (76.2 mm) diameter round horn and a 1:1 booster to create a porous film assembly. The anvil had 0.25 inch (6.4 mm) spacing, 0.044 inch (1118 μm) diameter pins, and a 0.01 inch (254 μm) pin height. Settings of 40 psi (0.28 Mpa), 1.5 second weld time and a 1.0 second hold time were used. The non-apertured side of the porous film assembly was laminated to a Tegaderm™ dressing and converted into 3.3 cm² parts. The release liner was then removed from the dried naltrexone coating of a 2.0 cm² part and laminated to the apertured film side of a 3.3 cm² part. Solvent extraction was determined using the test method described above. The results are shown in Table 1.

Example 2

A transdermal dosage form according to FIG. 3 was prepared as follows.

A dried fentanyl coating was prepared as described in Example 1.

An adverse agent or reservoir component was prepared as follows. Naltrexone (13.55g) was added to copolymer (149.4 g of a solution of a 28.6% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was 5.2 mg/cm².

The dried naltrexone coating was divided into 3 equal pieces. A 5-layer laminate of alternating dried naltrexone coatings and 3 mil (76 μm) thick polyvinyl alcohol (PVA) film (Monosol® M7030, Chris Craft Industrial Products, Inc., Gary, Ind.) was prepared by sequential lamination steps. The outer layers of the 5-layer laminate were dried naltrexone coatings. The silicone release liner was removed from one of the outer layers of the 5-layer laminate and the dried naltrexone coating was laminated to the ethylene vinyl acetate side of the dried fentanyl coating prepared above to form a multilaminate construction. The resulting multilaminate construction was converted into 2.0 cm² parts.

A 1.0 ounce/yd² (33.9 g/m²) basis weight porous polyethylene apertured film (Style 6007, Polymer Group, Inc., North Charleston, S.C.) was ultrasonically welded to a 3.0 mil (76 μm) thick polyethylene film (CoTran™9720, 3M, St. Paul, Minn.) using a 20 kHz Dukane ultrasonic welder with a 3 inch (76.2 mm) diameter round horn and a 1:1 booster to create a porous film assembly. The anvil had 0.25 inch (6.4 mm) spacing, 0.044 inch (1118 μm) diameter pins, and a 0.01 inch (254 μm) pin height. Settings of 40 psi (0.28 Mpa), 1.5 second weld time and a 1.0 second hold time were used. The non-apertured side of the porous film assembly was laminated to a Tegaderm™ dressing and converted into 3.3 cm² parts. The release liner was then removed from the dried naltrexone coating of a 2.0 cm² part and laminated to the apertured film side of a 3.3 cm² part. Solvent extraction was determined using the test method described above. The results are shown in Table 1.

Example 3

A transdermal dosage form was prepared according to the same general description as Example 1 with the exception that the dried fentanyl coating had a coating weight of 8.0 mg/cm² and contained 9.6 percent fentanyl. Solvent extraction in buffered saline was determined using the test method described above. The results are shown in Table 1.

Example 4

A transdermal dosage form was prepared according to the same general description as Example 1 with the exception that the dried fentanyl coating had a coating weight of 18.6 mg/cm². Solvent extraction in buffered saline was determined using the test method described above. The results are shown in Table 1.

TABLE I

| | | Solvent Extraction | | | | | | | | |
|---|---|---|---|---|---|---|---|---|---|---|
| Example | | Ratio Fentanyl/ Naltrexone | | | Naltrexone Extracted [mg] | | | Fentanyl Extracted [mg] | | |
| Number | Solvent | 5 min | 15 min | 30 min | 5 min | 15 min | 30 min | 5 min | 15 min | 30 min |
| 1 | DI Water | 0.5 | 0.4 | 0.3 | 0.2 | 0.5 | 0.8 | 0.1 | 0.2 | 0.3 |
| 1 | PBS | 2.1 | 1.6 | 1.3 | 0.1 | 0.2 | 0.3 | 0.1 | 0.2 | 0.4 |
| 1 | Ethanol | 8.2 | 2.5 | 1.1 | 0.3 | 1.0 | 2.3 | 2.1 | 2.1 | 2.2 |
| 1 | Ethyl Acetate | 5.6 | 3.0 | 2.1 | 0.8 | 0.8 | 1.1 | 3.9 | 2.6 | 2.5 |
| 1 | Diethyl Ether | 3.9 | 2.5 | 1.9 | 0.5 | 0.8 | 1.0 | 2.4 | 2.3 | 2.3 |
| 2 | DI Water | 0.4 | 0.4 | 0.4 | 0.2 | 0.4 | 0.7 | 0.1 | 0.2 | 0.3 |
| 2 | PBS | 1.0 | 1.1 | 0.9 | 0.1 | 0.2 | 0.4 | 0.1 | 0.2 | 0.3 |
| 2 | Ethanol | 4.2 | 1.4 | 1.2 | 0.7 | 1.5 | 1.7 | 2.2 | 2.2 | 2.2 |
| 2 | Ethyl Acetate | 3.3 | 1.9 | 1.6 | 0.8 | 1.4 | 1.7 | 2.6 | 2.6 | 2.5 |
| 2 | Diethyl Ether | 3.2 | 1.8 | 1.4 | 0.8 | 1.7 | 1.8 | 2.4 | 3.1 | 2.5 |
| 3 | PBS | 0.8 | 0.7 | 0.6 | 0.1 | 0.3 | 0.4 | 0.1 | 0.2 | 0.2 |
| 4 | PBS | 1.1 | 1.2 | 1.1 | 0.1 | 0.2 | 0.3 | 0.2 | 0.3 | 0.4 |

Example 5

A transdermal dosage form according to FIG. 1 was prepared as follows. Dried fentanyl and naltrexone coatings were prepared according to the same general description as in Example 1 with the exception that the dried fentanyl coating had a coating weight of 14.4 mg/cm² and the dried naltrexone coating had a coating weight of 11.4 mg/cm².

The multilaminate construction prepared by laminating the dried naltrexone coating to the ethylene vinyl acetate side of the dried fentanyl coating was converted into 10.5 cm² parts.

A 1.0 ounce/yd² (33.9 g/m²) basis weight porous polyethylene apertured film (Style 6007, Polymer Group, Inc., North Charleston, S.C.) was converted into 10.5 cm² parts. A 3.0 mil (76 µm) thick polyethylene film (CoTran™9720, 3M, St. Paul, Minn.) was converted into 20.0 cm² parts. Each 10.5 cm² apertured film part was ultrasonically welded to a 20.0 cm² polyethylene film part to form a porous film assembly using a 20 kHz Dukane ultrasonic welder with a 3 inch (76.2 mm) diameter round horn and a 1:1 booster. The anvil had 0.25 inch (6.4 mm) spacing, 0.044 inch (1118 µm) diameter pins, and a 0.01 inch (254 µm) pin height. Settings of 40 psi (0.28 Mpa), 25 second weld time and a 0.5 second hold time were used.

A dried adhesive coating was prepared by coating a copolymer solution (isooctyl acrylate/acrylic acid, 97:3, 31.8% solids, inherent viscosity of 1.11) onto a silicone release liner and drying to obtain a dried coating weight of 3.5 mg/cm². The dried adhesive coating was converted into ring shaped parts with an outer diameter of 5.05 cm and an inside diameter of 3.66 cm. These ring shaped parts were then adhered to the polyethylene film portion of the porous film assembly prepared above such that the adhesive surrounded the apertured film portion of the porous film assembly.

The dried naltrexone coating of the 10.5 cm² fentanyl and naltrexone containing laminates prepared above were laminated to the apertured film portion of the porous film assembly to prepare a finished transdermal delivery patch. The resulting patches had a total area of 20.0 cm² and an active drug-containing area of 10.5 cm². Mechanical separation testing was performed as described in the method above. The results are shown in Table 2.

Example 6

A transdermal dosage form was prepared according to the same general description as Example 5 with the exception that the naltrexone reservoir layer was a 5-layer laminate of alternating dried naltrexone coatings and PVA layers as described in Example 2. Mechanical separation testing was performed as described in the method above. The results are shown in Table 2.

TABLE 2

Mechanical Separation

| Example Number | Fentanyl [mg/device] | Naltrexone [mg/device] | Ratio Fentanyl/Naltrexone |
|---|---|---|---|
| 5 | 6.2 | 3.7 | 1.7 |
| 6 | 8.5 | 5.4 | 1.6 |

Example 7

A transdermal dosage form according to FIG. 1 was prepared as follows.

Fentanyl (3.44 g) was added to methanol (3.99 g) and mixed until all of the fentanyl was dissolved. To this solution, methyl laurate (5.01 g) and copolymer (29.8 g of a 38.8% solids solution of isooctyl acrylate/2-hydroxyethyl acrylate/Elvacite™ 1010 with an inherent viscosity of 0.63 dL/g prepared according to the general procedure described for Copolymer A above) was added and mixed until a uniform coating formulation was obtained. The coating formulation was knife coated onto a silicone release liner. The coated liner was oven dried for 4 minutes at 110° F. (43° C.), for 4 minutes at 185° F. (85° C.), and for 2 minutes at 200° F. (93.3° C.). The resulting dried coating weight was approximately 12.6 mg/cm². The resulting coating contained 17.2 percent fentanyl. The coated liner was laminated onto the polyethylene terephthalate side of a 2.0 mil (51 µm) thick laminate film of polyethylene terephthalate and ethylene vinyl acetate (Scotchpak™ 9732, 3M, St. Paul, Minn.).

An adverse agent or reservoir component was prepared as follows. Naltrexone (3.00 g) was added to copolymer (59.5 g of a 28.6% solids solution of 2-ethylhexyl acrylate/dimethylaminoethyl acrylate methyl chloride quaternary/methoxy polyethylene glycol 400 acrylate prepared according to the general procedure described for copolymer B above) and mixed until homogeneous. The coating formulation was knife coated onto a silicone release liner. The coated liner was oven dried for 4 minutes at 110° F. (43° C.), for 2 minutes at 185° F. (85° C.), and for 2 minutes at 200° F. (93.3° C.) to prepare a dried naltrexone coating. The resulting dried coating weight was approximately 14.8 mg/cm². The coated liner was laminated to the ethylene vinyl acetate side of the dried fentanyl coating prepared above to form a multilaminate construction. The resulting multilaminate construction was converted into 2.0 cm² parts.

A porous film assembly with a ring shaped adhesive coating was prepared and adhered to the 2.0 cm² multilaminate parts following the general description in Example 5 with the exception that the final dimension of the finished transdermal patches had a total area of 5.0 cm² and an active drug-containing area of 2.0 cm². Permeation of both fentanyl and naltrexone through human cadaver skin was determined using the test method described above. The results are shown in Tables 3 and 4.

Example 8

A transdermal dosage form was prepared according to the same general description as in Example 7 with the exception that the dried fentanyl coating was prepared as described in Example 5. Permeation of both fentanyl and naltrexone through human cadaver skin was determined using the test method described above. The results are shown in Table 3 and 4.

TABLE 3

Human Cadaver Skin Permeation

| Example Number | Average Flux Fentanyl (µg/cm²/hr) | | | | | | | | | | |
|---|---|---|---|---|---|---|---|---|---|---|---|
| | 4 hr | 8 hr | 12 hr | 24 hr | 36 hr | 48 hr | 72 hr | 96 hr | 120 hr | 144 hr | 168 hr |
| 7 | 0.0 | 0.9 | 3.6 | 4.6 | 4.8 | 5.3 | 4.7 | 4.7 | 4.2 | 3.8 | 3.6 |
| 8 | 0.5 | 0.4 | 0.5 | 1.7 | 1.9 | 2.2 | 2.1 | 2.2 | 2.2 | 2.1 | 1.9 |

TABLE 4

Human Cadaver Skin Permeation

Average Flux Naltrexone (μg/cm²/hr)

| Example Number | 4 hr | 8 hr | 12 hr | 24 hr | 36 hr | 48 hr | 72 hr | 96 hr | 120 hr | 144 hr | 168 hr |
|---|---|---|---|---|---|---|---|---|---|---|---|
| 7 | 0.00 | 0.00 | 0.00 | 0.00 | 0.00 | 0.00 | 0.00 | 0.00 | 0.00 | 0.00 | 0.00 |
| 8 | 0.00 | 0.00 | 0.00 | 0.00 | 0.00 | 0.00 | 0.60 | 0.00 | 0.28 | 0.00 | 0.12 |

The present invention has been described with reference to several embodiments thereof. The foregoing detailed description and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention should not be limited to the exact details of the compositions and structures described herein, but rather by the language of the claims that follow.

We claim:

1. A transdermal dosage form comprising:
   an active agent component comprising a polymeric material and an active agent, wherein the active agent component has a proximal, skin-contacting surface and a distal surface opposed to the proximal surface;
   an overlay backing;
   an adverse agent component comprising an antagonist to the abusable drug substance, wherein the adverse agent component is interposed between the distal surface of the active agent component and the overlay backing; and
   a porous material adjacent to and adjoining the adverse agent component;
   wherein the porous material is in fluid communication with the proximal surface of the active agent component.

2. A transdermal dosage form according to claim 1, further comprising a barrier interposed between the active agent component and the adverse agent component.

3. A transdermal dosage form according to claim 2, further comprising an adhesive material connecting the adverse agent component and the barrier layer.

4. A transdermal dosage form according to claim 2, further comprising an adhesive material connecting the porous material and the overlay backing.

5. A transdermal dosage form according to claim 2, wherein the polymeric material of the active agent component comprises an acrylate pressure-sensitive adhesive.

6. A transdermal dosage form according to claim 2, wherein the adverse agent component comprises a polymeric material.

7. A transdermal dosage form according to claim 6, wherein the adverse agent component comprises a pressure-sensitive adhesive.

8. A transdermal dosage form according to claim 6, wherein the adverse agent component comprises a microporous film.

9. A transdermal dosage form according to claim 1, wherein the adverse agent component is interposed between the distal surface of the active agent component and the porous material.

10. A transdermal dosage form according to claim 1, wherein the adverse agent component is interposed between the porous material and the overlay backing.

11. A transdermal dosage form according to claim 1, wherein at least a portion of the overlay backing extending beyond the active agent component is coated with a pressure sensitive adhesive.

12. A transdermal dosage form according to claim 11, wherein the overlay backing is a continuous, polymeric film.

13. A transdermal dosage form according to claim 12, wherein the overlay backing comprises a polymer selected from the group consisting of polyethylene, polypropylene, and polyurethane.

14. A transdermal dosage form according to claim 1, wherein the antagonist comprises a narcotic antagonist.

15. A transdermal dosage form according to claim 14, wherein the antagonist is selected from the group consisting of naltrexone, naloxone, and nalbuphine.

16. A transdermal dosage form according to claim 1, wherein the active agent is a narcotic.

17. A transdermal dosage form according to claim 16, wherein the active agent is fentanyl.

18. A transdermal dosage form comprising:
   a release liner;
   an overlay backing;
   an active agent component interposed between the release liner and the overlay backing, wherein the active agent is in diffusional communication with the release liner;
   a barrier interposed between the active agent component and the overlay backing;
   an adverse agent component comprising an antagonist to the active agent, wherein the adverse agent component is interposed between the barrier and the overlay backing; and
   a porous material adjacent to and adjoining the adverse agent component;
   wherein the porous material is in fluid communication with the release liner.

19. A transdermal dosage form according to claim 18, wherein the active agent component comprises an acrylate copolymer pressure sensitive adhesive.

20. A transdermal dosage form according to claim 18, further comprising an adhesive layer connecting the porous material and the overlay backing.

21. A transdermal dosage form according to claim 18, wherein the adverse agent component comprises a polymer.

22. A transdermal dosage form according to claim 21, wherein the adverse agent component comprises a pressure-sensitive adhesive.

23. A transdermal dosage form according to claim 21, wherein the adverse agent component comprises a microporous film.

24. A transdermal dosage form according to claim 18, wherein at least a portion of the overlay backing extending beyond the active agent component is coated with a pressure sensitive adhesive.

25. A transdermal dosage form according to claim 24, wherein the overlay backing is a continuous, polymeric film.

26. A transdermal dosage form according to claim 25, wherein the overlay backing comprises a polymer selected from the group consisting of polyethylene, polypropylene, and polyurethane.

27. A transdermal dosage form according to claim 18, wherein the antagonist comprises a narcotic antagonist.

28. A transdermal dosage form according to claim 27, wherein the antagonist is selected from the group consisting of naltrexone, naloxone, and nalbuphine.

29. A method of transdermal delivery of an active agent from a tamper-resistant dosage form comprising:
   a) providing a transdermal dosage form according to claim 1; and
   b) applying the dosage form to a portion of the skin or mucosa of a patient for a period sufficient to achieve the desired therapeutic result.

30. A method of transdermal delivery of an active agent from a tamper-resistant dosage form comprising:
   a) providing a transdermal dosage form according to claim 18; and
   b) applying the dosage form to a portion of the skin or mucosa of a patient for a period sufficient to achieve the desired therapeutic result.

* * * * *